United States Patent [19]
Giroux et al.

[11] Patent Number: 5,994,134
[45] Date of Patent: Nov. 30, 1999

[54] VIRAL PRODUCTION PROCESS

[75] Inventors: Daniel D. Giroux, La Jolla; Ann M. Goudreau; Muralidhara Ramachandra, both of San Diego; Paul W. Shabram, Olivenhain, all of Calif.

[73] Assignee: Canji, Inc., San Diego, Calif.

[21] Appl. No.: 09/073,076

[22] Filed: May 4, 1998

[51] Int. Cl.[6] ...................................................... C12N 7/01
[52] U.S. Cl. ............................ 435/403; 435/41; 435/174; 435/177; 435/235.1; 435/239; 435/325; 435/366; 435/369; 435/395; 435/289.1; 435/948
[58] Field of Search ............................ 435/41, 174, 177, 435/235.1, 239, 325, 366, 369, 395, 403, 289.1, 948

[56] References Cited

U.S. PATENT DOCUMENTS

5,219,752  6/1993  Takazawa et al. .
5,494,811  2/1996  Scott et al. .

*Primary Examiner*—Jeffrey Stucker
*Attorney, Agent, or Firm*—Richard B. Murphy

[57] ABSTRACT

The present invention is directed to a method of producing recombinant viral vectors at high titers incorporating a variety of important advancements over the art. The method of the present invention incorporates multiple features which provide enhanced production of viruses, particularly those viruses encoding exogenous transgenes. The specifically illustrated method describes a method for the high titer serum-free media production of recombinant replication defective adenoviruses containing an exogenous transgene. The invention provides methods of preparing microcarriers, methods for seeding bioreactors at high cell density, increasing the infectivity of the producer cells to the virus, methods to increase product yield through synchronization of the cell cycle of the producer cells, and methods to minimize the deleterious effects of exogenous transgenes. The invention further provides producer cells prepared by the process of the invention. The invention further provides viruses produced by the process.

17 Claims, 3 Drawing Sheets

VIRAL PRODUCTION PROCESS

BACKGROUND OF THE INVENTION

A variety of in vivo gene therapy products currently under development are based on the delivery of a therapeutic transgene by recombinant viral vectors. A common vehicle for the delivery of transgenes are recombinant adenoviruses, usually those deficient for replication in any cell other than a specific packaging cell line. These packaging cell lines express certain adenoviral genes necessary for virus replication that have been deleted in the deficient virus. For the production of adenoviruses containing deletions in the E1 region, the most commonly used cell line is the 293 cell line. The production of replication deficient adenovirus in 293 cells is difficult because the cell line is difficult to grow. For example, 293 cells require attachment to a substrate and appear to differentiate at high confluency. Another limitation is that replication deficient adenoviruses do not replicate as well as wild type viruses. While the specific virus production for wild type adenoviruses in 293 cells is approximately 80,000–100,000 particles per cell, E1 replication deficient adenoviruses typically produce only 100–2000 particles per cell. Based on current assessments of dosage regimens and therapeutic market size, estimates have indicated that annual production of approximately $10^{18}$ particles will be necessary to satisfy demand for some gene therapy products. Improvements in the production of recombinant adenoviruses to levels which will satisfy the anticipated market for adenoviral gene therapy products is therefore required to make this technology commercially feasible.

The present invention describes a microcarrier based process for the production of viral vectors in anchorage dependent packaging cell lines, which allows for cost-effective production of adenoviral gene therapy products sufficient to meet the projected market demand. The invention describes a scaleable production process which produces greater than $2 \times 10^{15}$ viral particles in a 5 liter bioreactor. This process is fully scaleable to achieve the projected $10^{18}$ particles per year with a bioreactor as small as 100 liters and 5 liter purification columns.

SUMMARY OF THE INVENTION

The present invention is directed to a method of producing recombinant viral vectors at high titers incorporating a variety of important advancements over the art. The method of the present invention incorporates multiple features which provide enhanced production of viruses, particularly those viruses encoding exogenous transgenes. The specifically illustrated method describes a method for the high titer serum-free media production of recombinant replication defective adenoviruses containing an exogenous transgene. The invention provides methods of preparing microcarriers, methods for seeding bioreactors at high cell density, increasing the infectivity of the producer cells to the virus, methods to increase product yield through synchronization of the cell cycle of the producer cells, and methods to minimize the deleterious effects of exogenous transgenes. The invention further provides producer cells prepared by the process of the invention. The invention further provides viruses produced by the process.

DETAILED DESCRIPTION OF THE INVENTION

All publications, patents and patent applications cited in this specification are herein incorporated by reference in their entirety as if each individual publication, patent or patent application were specifically and individually indicated to be incorporated by reference. The use of the singular with specific terms also implies the use of the plural and vice versa. The headings are included merely for convenience and are not intended to be limiting in the scope of the disclosure.

The production of virus by mammalian cell culture is dependent upon a variety of factors. As described below, a variety of techniques can be employed to improve the virus production within a given producer cell, such as synchronization of the producer cells, increasing infectivity of the producer cells, and suppressing the effects of transgenes during culture. Although it is theoretically feasible to produce large amounts of viral particles by expanding the scale of the production facility or by the repetition of low yield processes, these factors combine to defeat the commercial practicality of such approaches. Consequently, the overall efficiency of the process in a given volume is, in large part, dependent on the concentration of cells which can be effectively maintained in a given volume of media. If one can achieve a high concentration of viable producer cells in a given volume, combined with high intracellular virus production, the overall efficiency of the process is improved to make the process economical.

I. Achieving a High Cell Density in a Microcarrier Based Reactor

The present invention provides a method of achieving a cell density greater than $5 \times 10^6$ producer cells/ml in a microcarrier based bioreactor process for the production of a virus in a producer cell, said method comprising the steps of:

a) preparing a culture of producer cells attached to microcarriers wherein the ratio of producer cells to microcarriers is approximately 10 cells/microcarrier b) seeding the bioreactor with a quantity of the producer cell-coated microcarriers prepared in step (a) to a density of greater than approximately 6 grams (based on the dry weight of the microcarrier) of producer cell-coated microcarriers per liter of bioreactor media volume; and c) culturing the producer cells in the bioreactor under perfusion conditions in serum containing media to a density of greater than 100 cells/microcarrier.

Bioreactor

The term "bioreactor" refers to a device for cell culture containing a vessel where the cell culture is maintained. The design of the bioreactor should ensure sterility and provide for containment of the genetically engineered producer cell and virus. A variety of bioreactors are commercially available for the culture of anchorage dependent producer cells and suspension cultures and are well known to those of skill in the art and may be readily adapted to the practice of the present invention. Bioreactors are preferably equipped with an agitation system to keep the contents uniformly mixed and to facilitate oxygen transfer. Preferably, the bioreactor includes sensors that permit monitoring and manipulation of as many process parameters (temperature, pH, dissolved oxygen) as possible so that these parameters can be maintained within optimal ranges for cell growth. A bioreactor in the preferred practice of the invention contains an apparatus to oxygenate the media that is separate from the microcarrier bed. A preferred bioreactor useful in the practice of the present invention is the CelliGen Plus® bioreactor equipped with the Cell-Lift® impeller for low shear and high oxygenation in microcarrier cultures commercially available from New Brunswick Scientific Company, Inc., 44 Talmadge Road, Edison, N.J., U.S.A. 08818-4005. Certain modifications, such as a cell settling tube or a decanting column, may be employed to facilitate ease of manipulation of the culture (commercially available from New Brunswick Scientific).

Viruses and Viral Vectors

The terms virus(es) and vector(s) are used interchangeably herein. The term "particles" or "viral particles" refers to virions or envelopes into which the viral genome is packaged. The viruses to be produced by the practice of the present invention include recombinantly modified enveloped or non-enveloped DNA and RNA viruses, preferably selected from baculoviridiae, parvoviridiae, picornoviridiae, herpesveridiae, poxviridae, adenoviridiae, or picomnaviridiae. The viruses may be naturally occurring viruses or their viral genomes may be modified by recombinant DNA techniques to include expression of exogenous transgenes and may be engineered to be replication deficient, conditionally replicating or replication competent. Chimeric vectors which exploit advantageous elements of each of the parent vector properties (See e.g., Feng, et al.(1997) Nature Biotechnology 15:866–870) may also be produced by the methods described herein. Minimal vector systems in which the viral backbone contains only the sequences need for packaging of the viral vector and may optionally include a transgene expression cassette may also be produced according to the practice of the present invention. The present invention is particularly useful in the preparation of viruses are derived from the adenoviral, adeno-associated viral and retroviral genomes. In the most preferred practice of the invention, the vectors to be produced are replication incompetent vectors derived from the human adenovirus genome. In the preferred practice of the invention, the vectors to be produced are replication deficient or conditionally replicating adenoviral vectors. In the most preferred practice of the invention as exemplified herein, the vectors to be produced are replication deficient (E1 defective/deleted) adenoviral vectors encoding an expression cassette for the exogenous tumor suppressor gene in a cell infected by the vector.

Conditionally replicating viral vectors are used to achieve selective expression in particular cell types while avoiding untoward broad spectrum infection. Examples of conditionally replicating vectors are described in Bischoff, et al. (1996) Science 274:373–376; Pennisi, E. (1996) Science 274:342–343; Russell, S. J. (1994) Eur. J. of Cancer 30A (8):1165–1171. Additionally, the viral genome may be modified to include inducible promoters which achieve replication or expression of the transgene only under certain conditions. Examples of inducible promoters are known in the scientific literature (See, e.g. Yoshida and Hamada (1997) Biochem. Biophys. Res. Comm. 230:426–430; Iida, et al. (1996) J. Virol. 70(9):6054–6059; Hwang, et al.(1997) J. Virol 71(9):7128–7131; Lee, et al. (1997) Mol. Cell. Biol. 17(9):5097–5105; and Dreher, et al.(1997) J. Biol. Chem 272(46); 29364–29371. The transgene may also be under control of a tissue specific promoter region allowing expression of the transgene only in particular cell types.

It may be valuable in some instances to utilize viruses which effect expression of the transgene in a particular cell type. Certain vectors exhibit a natural tropism for certain tissue types. For example, vectors derived from the genus herpesviridiae have been shown to have preferential infection of neuronal cells. Examples of recombinantly modified herpesviridiae vectors are disclosed in U.S. Pat. No. 5,328,688 issued Jul. 12, 1994. Cell type specificity or cell type targeting may also be achieved in vectors derived from viruses having characteristically broad infectivities by the modification of the viral envelope proteins. For example, cell targeting has been achieved with adenovirus vectors by selective modification of the viral genome knob and fiber coding sequences to achieve expression of modified knob and fiber domains having specific interaction with unique cell surface receptors. Examples of such modifications are described in Wickham, et al.(1997) J. Virol 71(11): 8221–8229 (incorporation of RGD peptides into adenoviral fiber proteins); Arnberg, et al.(1997) Virology 227:239–244 (modification of adenoviral fiber genes to achieve tropism to the eye and genital tract); Harris and Lemoine (1996) TIG 12(10):400–405; Stevenson, et al.(1997) J. Virol. 71(6):4782–4790; Michael, et al.(995) Gene Therapy 2:660–668 (incorporation of gastrin releasing peptide fragment into adenovirus fiber protein); and Ohno, et al.(1997) Nature Biotechnology 15:763–767 (incorporation of Protein A-IgG binding domain into Sindbis virus). Other methods of cell specific targeting have been achieved by the conjugation of antibodies or antibody fragments to the envelope proteins (see, e.g. Michael, et al. (1993) J. Biol. Chem 268:6866–6869, Watkins, et al. (1997) Gene Therapy 4:1004–1012; Douglas, et al.(1996) Nature Biotechnology 14: 1574–1578. Alternatively, particular moieties may be conjugated to the viral surface to achieve targeting (See, e.g. Nilson, et al. (1996) Gene Therapy 3:280–286 (conjugation of EGF to retroviral proteins). These recombinantly modified vectors may be produced in accordance with the practice of the present invention.

In the preferred practice of the invention, the virus to be produced is derived from genus adenoviridiae. Particularly preferred viruses are derived from the human adenovirus type 2 or type 5. Such viruses are preferably replication deficient by modifications or deletions in the E1a and/or E1b coding regions. Other modifications to the viral genome to achieve particular expression characteristics or permit repeat administration or lower immune response are preferred. More preferred are recombinant adenoviruses having complete or partial deletions of the E4 coding region, optionally retaining E4orf6 and E4orf6/7. The E3 coding sequence may be deleted but is preferably retained. In particular, it is preferred that the promoter operator region of E3 be modified to increase expression of E3 to achieve a more favorable immunological profile for the therapeutic vectors. Most preferred are human adenoviral type 5 vectors containing a DNA sequence encoding p53 under control of the cytomegalovirus promoter region and the tripartite leader sequence having E3 under control of the CMV promoter and deletion of E4 coding regions while retaining E4orf6 and E4orf6/7. In the most preferred practice of the invention as exemplified herein, the vector is ACN53, as described in Wills, et al. (1994) Human Gene Therapy 5:1079–1088.

Producer Cells

The term "producer cell" is used herein to describe an anchorage dependent viral packaging cell line. Anchorage dependent cells, or cultures derived from them, are those that will grow, survive, or maintain function optimally when attached to a surface such as glass or plastic. The use of this term does not imply that the cells are normal or that they are or are not neoplastically transformed. Dependent on the nature of the virus to be propagated, the genome of the cell line may be modified to complement deletions in the viral genome used as the vector. Where the vector is replication competent, any of the anchorage dependent cell lines commonly used for mammalian cell culture may be used as viral packaging cell lines. Examples of such anchorage dependent cell lines commonly used as viral vector packaging cell lines are HeLa or 293 cells (Graham and Smiley (1977) J. Gen. Virol. 36:59–72), and PERC.6 cells (as described in publication WO/97/00326, Application Serial No. PCT/NL96/00244).

In some applications, particularly when the virus is to be used for gene therapy applications, it is preferable that the vector be replication deficient (or replication defective) to avoid uncontrolled proliferation of the virus in the individual to be treated. In such instances mammalian cell lines are selected which have been engineered, either by modification of the producer cell's genome to encode essential viral functions or by the co-infection of the producer cell with a helper virus, to express proteins complementing the effect of the sequences deleted from the viral genome. For example, where the viral vector to be produced is the HIV-1 vector or a recombinantly modified derivative thereof, the HIV-1 packaging cell line, PSI422, may be used as described in Corbeau, et al. (1996) PNAS(U.S.A.) 93(24):14070–14075. Similiarly, where the viral vector to be produced is a retrovirus, the human 293-derived retroviral packaging cell line (293GPG) capable of producing high titers of retroviral particles may be employed as described in Ory, et al. (1996) PNAS(U.S.A.) 93(21):11400–11406. In the production of minimal vector systems, the producer cell is engineered (either by modification of the viral genome or by the use of helper virus or cosmid) to complement the functions of the parent virus enabling replication and packaging into virions in the producer cell line.

In the case where the virus to be produced is a recombinant adenovirus rendered replication deficient by the deletion of E1a and/or E1b functions, the 293 cell line is particularly preferred due to its ability to complement adenoviral E1a and E1b function. However, 293 cells may also be used for the expression of replication competent or conditionally replicating adenoviruses. Examples of other cell lines which may be used for the production of E1 defective adenoviruses are the PERC.6 cells (available from IntroGene, b.v., P.O. Box 2048, Leiden, Netherlands) which encode E1 in trans and has been demonstrated to possess excellent attachment to a microcarrier surface.

Transgenes

The recombinant vectors to be produced by the methods of the present invention may optionally contain a transgene expression cassette. The term expression cassette is used herein to define a nucleotide sequence (DNA or RNA) containing regulatory elements and a transgene coding sequence so as to effect the expression of the transgene in the target cell. Regulatory elements includes promoters, enhancers, transcription terminators, polyadenylation sites, etc. The term transgene embraces not only the sequence encoding the wild-type proteins and allelic variations but also homologous proteins sequences from other organisms, as well as any mutations or truncations, thereof which display essentially the same function as the wild-type polynucleotide or protein sequence. Examples of transgenes which may be included in such vectors include tumor suppressor genes, cyclin dependent kinase inhibitors, cytotoxic genes, cytostatic genes, proapoptotic genes, prodrug activating genes, tumor specific antigens, or antisense sequences. The term tumor suppressor genes (TSGs) refers to genes that when expressed in a target cell, are capable of suppressing the neoplastic phenotype. Examples of tumor specific antigens include MART1 and gp100 (Zhai, et al. (1997) J. immunotherapy 20:15–25). Examples of tumor suppressor genes include the retinoblastoma Rb gene and its variants Rb110 and Rb56, the MMAC-1 gene, the p53 gene, the DCC gene, the NF-1 gene, the erbA and erbb genes, p33, and p73. The term cyclin dependent kinase inhibitors includes the p27kip, p57kip2, p15ink4b, p18ink4c, p19ink4d, p16ink4a and p21sdi-1 genes. the term cytotoxic genes refers to genes which are designed to have a toxic effect in the target cell, either alone or in conjunction with exogenous chemical agents (e.g. pro-drug activating genes). Examples of such cytotoxic genes include DNA sequences encoding the cytotoxic domains of ricin, diphtheria, or pseudomonas exotoxin as well as the adenovirus E311.6 gene, adenovirus E1a. Examples of pro-drug activating genes include the thymidine kinase and cytosine deaminase genes. Pro-apoptotic genes includes p53 and p53 pathway genes (e.g. bax, bid, caspases, cytochrome c, etc.) and adenovirus E4orf4. Examples of other therapeutic transgenes which may be included in the vectors to be produced by the practice of the present invention include interferons (alpha, beta, gamma and consensus), interferon α2b E2F-Rb fusion proteins, interleukins (e.g. IL-2, IL-4, L-10), dopamine, serotonin, GABA, ACTH, and NGF.

Microcarrier(s)

The majority of animal cells used in the production of virus are anchorage-dependent and require attachment to a surface for optimal growth. In 1967 Van Wezel described the use of small particles (0.2 mm), microcarriers, for the growth of anchorage-dependent cells. These microcarriers are suspended in the culture medium by gentle agitation so that a homogeneous environment is obtained. Since the cells are located on the surface, they are subjected to mechanical stress and precautions must be taken to avoid shearing the cells from the surface during culture. Macroporous beads in which the anchorage-dependent cells have the possibility to utilize the interior surface may also be employed to reduce the possibility that shear forces may disrupt the cells to be cultured. However, such microcarriers do limit the surface area available for viral infection such that viral infection parameters should be adjusted. Microcarriers have been manufactured from different synthetic materials including dextran, polyacrylamide and polystyrene. Cell attachment to these charged microcarriers are mediated by ionic attractions. Many cell types have a cell surface protein, fibronectin, which has a biospecific binding to gelatin facilitating the use of gelatin coated microcarriers. An advantage to the use of gelatin is its susceptibility to degradation with proteolytic enzymes, which allows the release of the cells from the microcarriers with almost 100% viability by dissolution of the gelatin matrix with trypsin.

In the preferred practice of the invention, the microcarriers are Cytodex® microcarriers commercially available from Pharmacia Biotech AB, Uppsala, Sweden. Cytodex® microcarriers are based on cross-linked dextran beads. The beads are transparent, spherical and hydrated, and are substituted with positively charged groups. The microcarriers have a mean diameter of approximately 200 μm and a density of 1.03 g/cm3. Cytodex® has been derivatized to form three types; Cytodex® 3 is coated with collagen. In the preferred practice of the invention as exemplified herein, the microcarrier is Cytodex® 1.

Cytopore® microcarriers are based on a cross-linked cotton cellulose matrix. They are hydrophilic DEAE exchangers with a mean diameter of 230 μm and a density of 1.03 g/cm3. The microcarriers are transparent and are easily transported through tubing. Macroporous Cytopore® protects cells from shear forces generated by the stirrer or the aeration or spin filter. The matrix has an average pore size of 30 μm which enables cells to enter the interior of the microcarrier. Inside the microcarriers, cells are protected from shear forces from the stirrer, spin filter or bubbles created through sparging. The microporosity of Cytopore® facilitates nutrient supply to all sides of the cells.

Attachment of Cells to Microcarrier Surface

A culture of producer cells attached to microcarriers is produced when microcarriers contact the producer cells in a serum containing medium and are subjected to conditions which permit growth. The cells are grown in the presence of the microcarriers and produce new daughter cells, which are transferred to the exposed microcarrier surface by agitation of the culture. Upon completion of the process described, cells are concentrated to a high density of greater than 100 cells per microcarrier. This high concentration of cells on the microcarrier facilitates the high level production of virus.

In order to achieve high cell density and facilitate the attachment of daughter cells to microcarriers a variety of methods may be employed. Conditions should be designed to insure the efficient transfer of daughter cells to the microcarrier surface without dislodging the parent cell from the microcarrier surfaces. In the situation where there is a low initial quantity of producer cells, the cells may be microtriturated from the microcarriers by passing the coated microcarriers through an orifice at a low pressure (approximately 20 psi). The detached cells may then be used to evenly seed a greater number of microcarriers. Alternatively, one may also seed the bioreactor directly with a large quantity of cells. In the alternative, one may introduce the microcarriers to a medium containing flask. The microcarriers will sink to the bottom of the flask and cells are introduced to the flask which also sink and attach to the microcarrier surface. Slight agitation facilitates the attachment process. The concentration of cells on the microcarriers surface may readily determined by light microscopy.

As the cell culture is expanding, it is necessary to monitor and control culture parameters such as dissolved oxygen concentration, pH, temperature, and agitation. pH should be monitored throughout the cell growth process to ensure optimal conditions for cell replication. As the cells grow, metabolites are released into the medium, a process that can change medium pH. Therefore, the pH of the medium should be closely monitored and be adjusted by base or acid addition to maintain a relatively constant pH. The precise pH facilitating optimal growth will vary somewhat with the particular cell line, but is generally in the range of physiological pH. It is preferred for 293 cells that the pH in the cell culture be maintained in the range from about pH 6 to about pH 9, more preferably from about pH 7 to about pH 8, more preferably from about pH 7.2 to about 7.5, most preferably about pH 7.2.

Temperature is another physiological parameter that is to be monitored and controlled. Temperature in the cell culture should also be stabilized at the cell line's optimal growth temperature to achieve high cell density. Mammalian cells have an optimal temperature for growth. If grown at a temperature below the optimum, cellular growth occurs slowly. On the other hand, if the growth temperature is too high, cell death may occur. In the preferred practice of the invention, where the producer cell line is the 293 cell line, the temperature should be maintain below approximately 40° C., more preferably in the range from about 30° C. to about 38° C., most preferably about 37° C.

Seeding

The term "seeding" as described herein describes the introduction of the producer cells to the microcarrier bed volume. The coated microcarriers as prepared in Example 1, below, are then introduced into a bioreactor. The bioreactor is "seeded" with a quantity of the coated microcarriers of approximately 6 grams (based on the dry weight of the microcarrier) of coated microcarriers per liter of bioreactor volume. This is substantially greater than the recommended volume for the seeding of microcarriers in a given volume. The convention in the art is that the coated microcarriers should not occupy a volume greater than approximately 5% of the vessel/media volume, i.e. approximately 2 grams (based on the dry weight of the microcarrier) of coated microcarriers per liter of media/vessel volume. In the practice of the present invention, of approximately 10 grams (based on the dry weight of the microcarrier) the volume of settled coated microcarriers which comprises approximately 20% of the vessel volume. This high concentration of microcarriers contributes to high cell density in the ultimate culture of the recombinant virus and enhances viral yield. In order to achieve high yields in the practice of the present invention, the concentration of coated microcarriers should be from appoximately 6 to 25 grams (based on the dry weight of the microcarrier) per liter of reaction volume, preferably 6 to 15 grams, and most preferably about 10 grams (based on the dry weight of the microcarrier) per liter of reaction volume.

Growing Cells in Serum Containing Media to High Cell Density

The cells are then grown in the bioreactor under perfusion conditions. The culture of mammalian cells under perfusion conditions is well known in the art. However, it should be noted that certain parameters should be optimized to achieve maximum cell growth. For example, it is necessary to monitor oxygen content throughout the culture. Because oxygen is sparingly soluble in water (8.4 mg/L at 25° C.), it must be supplied continuously either in the form of sterilized air or pure oxygen, to the growing culture. Dissolved oxygen concentration should be maintained in the range of approximately 5% to about 200%, preferably from 50% to about 120%, most preferably about 100%. Dissolved oxygen concentration is defined as the point where 100% dissolved oxygen represents the oxygen concentration dissolved in medium in equilibrium with air. Oxygen concentration may be measured by conventional means such as a by dissolved oxygen monitoring probes commercially available from Instech Laboratories, Inc., 5209 Militia Hill Road, Plymouth Meeting Pa. 19462-1216 or Lazar Research Laboratories, Los Angeles Calif.

Adequate agitation of the bioreactor culture is essential to ensure an adequate supply of nutrients and to prevent the accumulation of toxic metabolites within the bioreactor.

Agitation of the medium also affects the rate of transfer of oxygen. Excessive agitation can cause mechanical damage to mammalian cells. Foaming should be avoided as the bubbling associated with the foaming process may generate sufficient shear forces within the culture to result in displacement of the cells from the microcarrier surface or lysis of the cells. Hence, a balance must be maintained between the need to provide good mixing and the need to avoid cell damage. In the preferred practice of the invention as exemplified herein using a 5 liter CelliGen Plus bioreactor, an agitation of approximately 70 rpm is maintained. In order to minimize foaming, the media is partitioned from the cells and oxygenated prior to re-introduction to the cells by the use of a sparging attachment to the bioreactor.

II. Production of Viral Particles in the Packaging Cell Line

The method of the invention further provides a method producing a population of producer cells containing a high titer of viral particles in a microcarrier based bioreactor in serum free media, said method comprising the process described above and further comprising the steps of:

d) removing the serum containing medium;
e) synchronizing the producer cells in G1 phase;
f) infecting the producer cells with a virus;
g) culturing cells under conditions to permit viral replication until a maximum point is achieved.

In order to prepare the bioreactor for the introduction of serum free media, one first allows the agitation in the bioreactor to cease. The microcarrier beads will then fall out of suspension and will settle at the bottom of the reactor volume, which allows the serum containing medium to be drained. The beads are then washed with serum free medium to minimize the percentage of serum containing medium. Washing is accomplished by restoring the microcarrier suspension to its original volume with serum free medium and achieving the thorough suspension of microcarriers by sufficient agitation. This medium was then drained as described above. This washing step may be repeated to achieve maximum removal of serum containing media.

Serum free medium in an amount sufficient to support the cell culture during infection is added to the cells. Serum free medium is defined as the growth medium for animal cell culture substantially free of animal derived sera. Serum free media are well known in the art (See, e.g. Freshney, R. I., *Culture of Mammalian Cells*, 1983, pp. 76–77). Alan R. Liss Company, New York). Simple serum free media may be supplemented with additional factors sufficient to enable the growth of cells. Alternatively, complete serum free media sufficient to support the growth of mammalian cells is commercially available from a variety of commercial suppliers. Examples of preferred serum free media include JRH Ex-Cell 525 serum free media (Catalog Number 61129-79P), CellGro Serum-free Media (commercially available form Gibco-BRL Life Sciences, Gaitherburg Md., U.S.A.), HyClone serum free media (#A-1111-L) commercially available from HyClone.

Media Additives

Serum-free media is frequently supplemented with one or more hormones such as insulin, transferrin, epidermal growth factor, hydrocortisone, etc. Serum free media may also be enhanced with additional agents to facilitate the growth of cells and may be dependent on the cell line used on the virus to be produced. For example, the media may be enhanced with TGF-beta or agents which upregulate endogenous transforming growth factor(TCGF)-beta in the cell. Alternatively, agents which upregulate or stabilize the viral binding receptors, such as the $\alpha v \beta 33$ and $\alpha v \beta 5$ integrins, may be added to the culture to improve infection efficiency.

In the most preferred practice of the invention as exemplified herein, the serum free media is Biowhittaker #12-604-F Dulbecco's Modified Eagle's Medium (DMEM) containing 1% CMF-1 (Applied Nutrient Sciences, Sorrento Valley, Calif.).

Suppression of Deleterious Transgenes

In the event that the recombinant virus uses a very strong promoter (e.g. CMV) for expression of the transgene, recombinant protein production will begin to compete with resources necessary for optimal viral replication. Consequently, it may be advantageous to add elements to the serum free media which down-regulate or inhibit the transgene promoter. For example, when the transgene promoter is the cytomegalovirus early promoter (CMV), elements such as neuramidase or tunicamycin may be added to suppress the CMV promoter during the culture.

Figure 1:
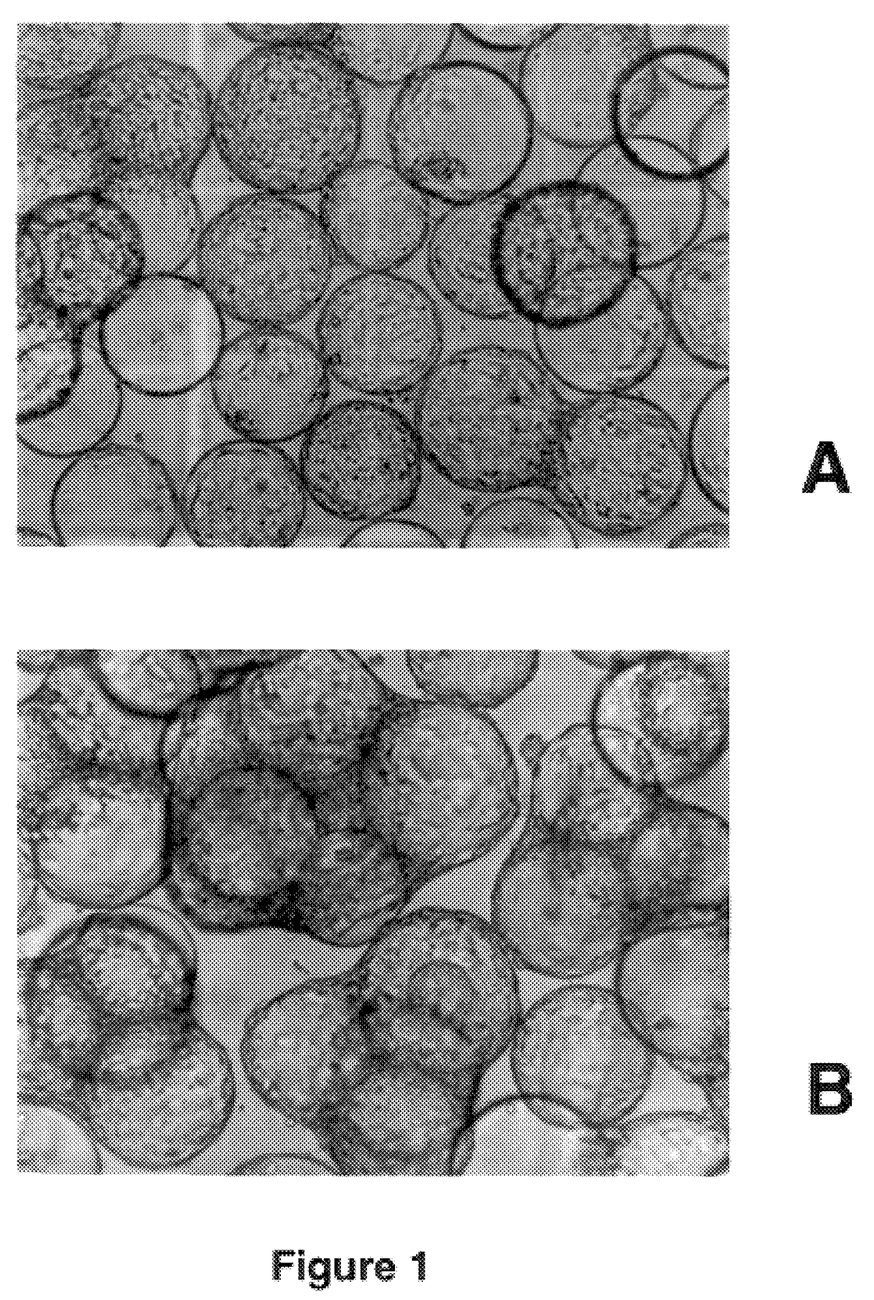
FIG. 1 is a photographic representation of microcarriers coated with cells examined under a light microscope. Panel A illustrates confluent microcarriers possessing approximately $10^6$ cells/ml or an average of approximately 23 cells per microcarrier. Panel B demonstrates the results of the super concentration of cells on the microcarriers of approximately $10^7$ cells/ml or an average of approximately 230 cells per microcarrier.
Figure 2:
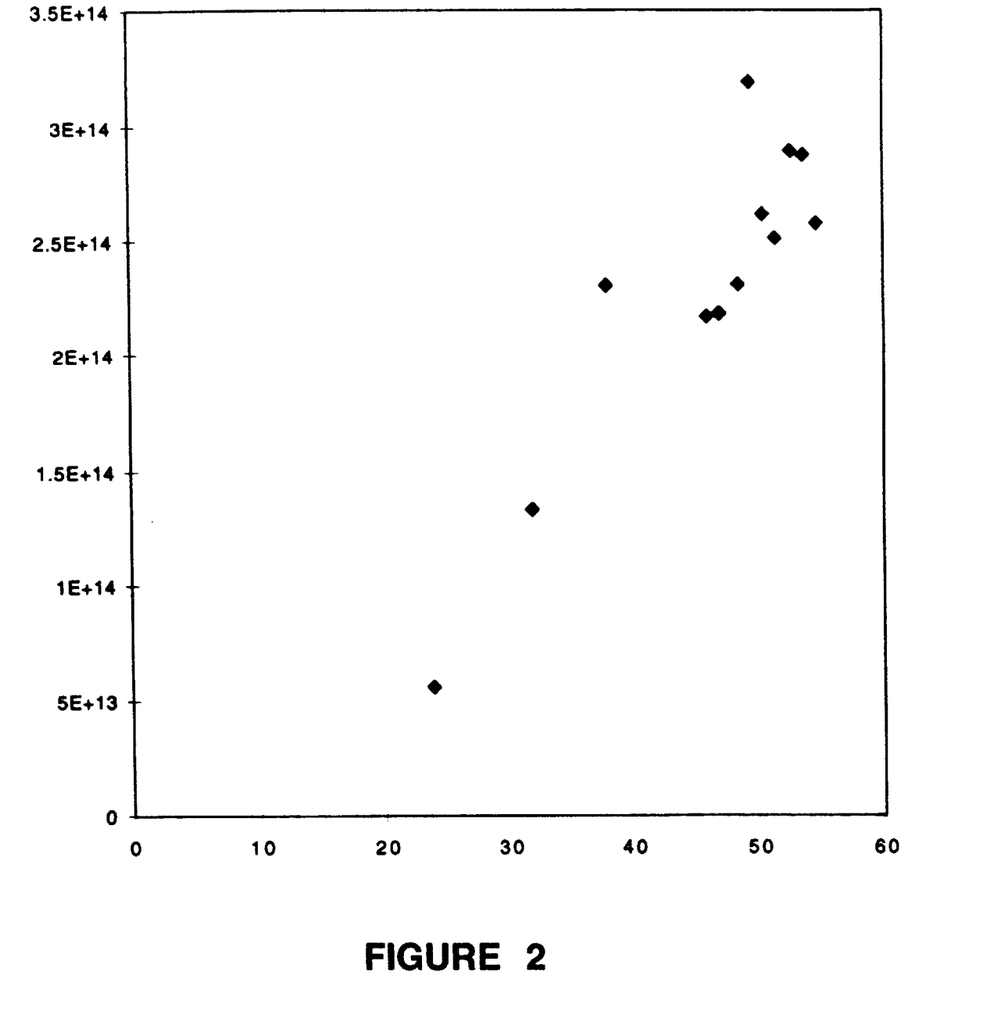
FIG. 2 is a graphical representation of the production levels of viral particles of ACN53 produced by the process described in Examples 1–5 herein. The vertical axis represents the total number of viral particles in the bioreactor. The horizontal axis represents the time post infection in hours. In this example $5 \times 10^6$ cells/ml were infected with virus resulting in the production of approximately 12,800 ACN53 viral particles per cell.
Figure 3:
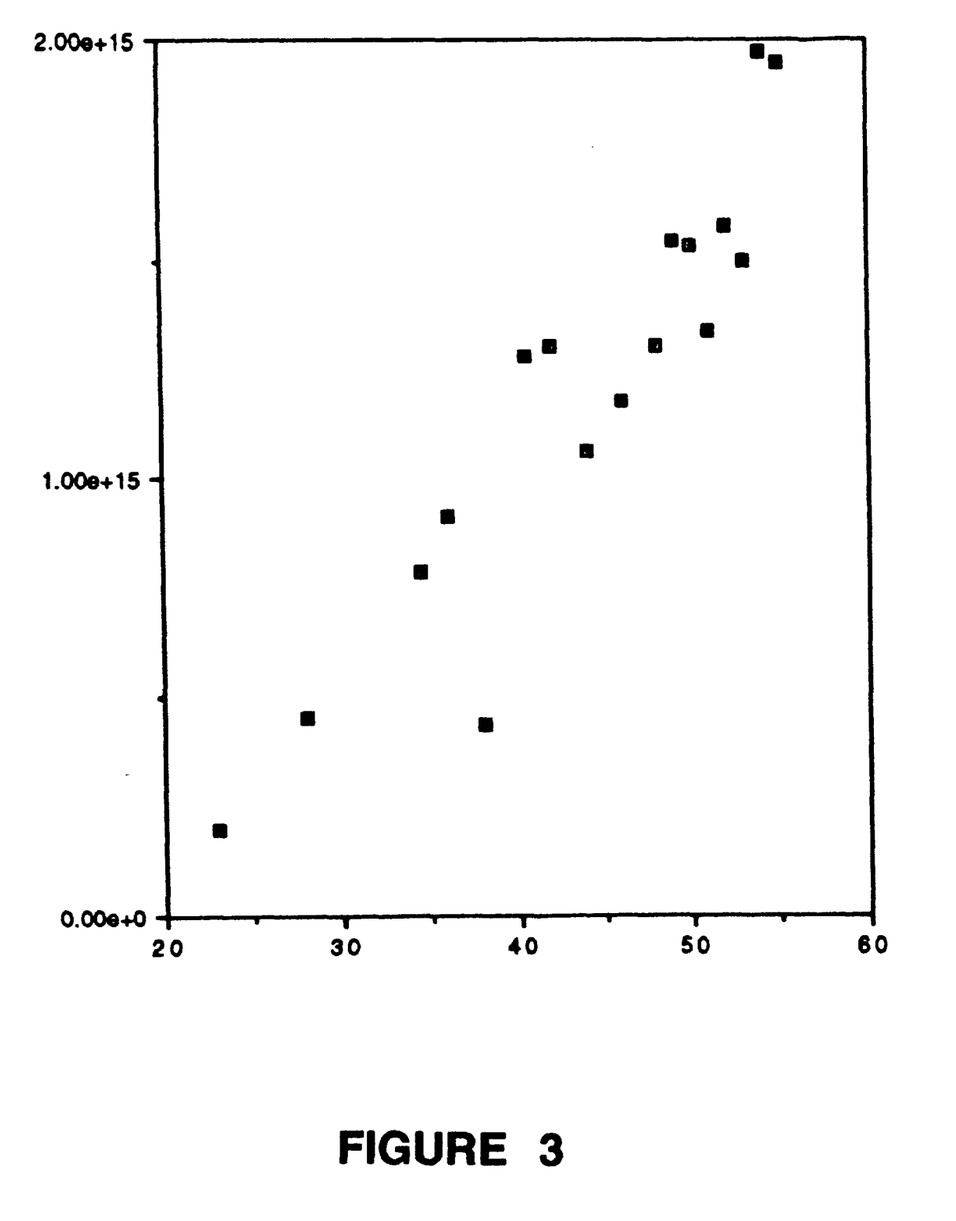
FIG. 3 is a graphical representation of the production of the ACN-Rb110 virus in substantial accordance with the teaching of Examples 1–5 herein. The vertical axis represents the total number of viral particles. The horizontal axis represents the time post infection in hours. This data demonstrates the production of approximately 39,000 ACN-Rb110 viral particles per cell.

Secondly, it is known that particular therapeutic transgenes may have a negative effect on the producer cell. For example, tumor suppressor genes such as p53 are known to induce apoptosis in normal cells with sufficient cell dosage. Consequently, viruses expressing such transgenes are particularly difficult to culture in high density. For example, a comparison of the yields from the practice of the present invention shown in FIGS. 2 and 3 demonstrates the significantly lower viral yield as a result of the expression of the p53 tumor suppressor gene. The present invention provides a method of minimizing the negative effect of a transgene toxic to the producer cell by the addition of an agent to the culture media in a concentration sufficient to inhibit the promoter driving the transgene. The agent to be added will be dependent on the promoter used to drive transgene expression but should not materially interfere with the expression of viral genes essential to viral replication. For example, the cytomegalovirus major immediate early promoter is a promoter commonly used to constitutively drive transgene expression. This promoter contains binding sites for the transcription factor NF-kB and requires the activated form of NF-kB for its activity. See e.g. Bellas, et al. (1995) J. Clinical Investigations 96:2521–27 and Loser, et al. (1998) J. Virology 72:180–190. In the presence of compounds that inhibit NF-kB activation, such as N-acetyl-L-cysteine or pentoxifylline, the activity of CMV promoter can be repressed to background levels (Bellas, et al. supra). Thus transient repression of the CMV promoter by the addition of such agents to the cultures during the production phase of recombinant viruses encoding CMV-promoter driven cytotoxic/cytostatic transgenes will improve yield of such viruses. Effective concentrations of N-acetyl. L-cysteine and pentoxitylline are from approximately 10 to 30 mM and from 0.5 to 3.0 mM respectively. Similarly, inhibitors of NF-kB activity are useful to prevent transgene expression in situations where the HIV-1-LTR is used to drive expression of the transgene (Mhashilkar, et al, J. Virology 71:6486–6494). Examples of agents capable of suppressing the action of other promoters and their effective concentration ranges are known in the art and may be substituted into the practice of the invention.

In the case where the cytotoxic/cytostatic transgene under the control of a promoter active in only (or primarily)a particular cell type, it is preferred that one employ a producer cell line in which the cell (or tissue) specific promoter is inactive. For example, where the promoter is active only in liver cells (see eg. $\alpha$-fetoprotein promoter (Huber et al., PNAS 88:8039–8043) the producer cell line is preferably not derived from a liver cell line. Additionally, in the case of inducible promoters as described above, it is preferred that the culture conditions (chemical composition, temperature, etc.) be maintained so as to prevent expression of the transgene from the inducible promoter.

It will be readily apparent to those of skill in the art that the foregoing procedure to suppress the effect of the transgene by may be applied to any procedure for eucaryotic cell culture including but not limited to microcarrier-based culture, suspension culture, spinner culture, and so-called "roller bottle" culture of cells.

Synchronization

In order to achieve maximum yield, it is preferred that the cells be synchronized in G1 phase prior to infection with the recombinant virus. By holding the cells in G1 phase, they are optimally prepared to be pushed into S phase, where nucleic acid synthesis primarily occurs. By synchronizing the cells, one achieves peak intracellular viral production. In the absence of synchronization, the subpopulation of producer cells advanced in the cell cycle will experience viral cell lysis prior to the optimal harvest point. These virions, which are spewed into the bioreactor supernatant, will be lost upon cell harvest. Similarly, cells which are lagging behind G1 phase will not reach optimal viral titers at the time of harvest.

Alternatively, another mechanism for improved virus production by synchronization of the producer cells is the stability of the virus or unencapsidated viral DNA post infection. It has been shown, for example, that retroviruses have a half-life of 4–6 hours post infection and that higher infection rates are observable when the cells are synchronized. Andreadis, et al. (1997) J. Virol. 71:7541–8; Andreadis, et al.(1998) Biotechnology and Bioengineering 58:272–281; Andreadis, et al.(1996) J. Theor. Biol. 182:1–20.

A variety of means may be employed to synchronize the cells in G1 phase. Holding the producer cells in serum free media will synchronize the cells in G0/G1 phase. Optimally, one holds the cells in serum free media for approximately one-third of a cell cycle (approximately 6–8 hours) in order to fully synchronize the cells. Alternatively, agents may be added which synchronize the cells. Examples of such agents include TGF-beta which produces cell cycle arrest at the G1/S interface. Similarly, inhibitors of phosphatidyl inositol 3-kinase (e.g. wortmannin and LY294002 (Eli Lilly and Company)) will block cells in G1 phase. Bacqueville, et al. (1998) Biochem. Biophys. Res. Comm. 244:630–636. Additionally, proteasome inhibitors such as lactacystin and/or N-carbobenzoxy-L-leucyl-L-leucyl-L-norvalinal have been demonstrated to induce cell cycle arrest in the G1 and G2 phases of the cell cycle. Mutomba, et al. (1997) Mol. Biochem. Parisitol. 90:491–504. Examples of other compounds which may be added to synchronize the cells include mimosine and aphidicolin (Oncogene (1997) 15(22) 2749–2753), quercetin (Shen and Webber (1997) Oncol. Res. 9:597–602), epirubicin (Hedenfalk, et al (1997) Cytometry 29(4):321–327) and lovastatin (Molecular and Cellular Biology (1985) 6(9):1197–1213).

It will be readily apparent to those of skill in the art that the foregoing procedure to increase yield by the synchronization of the cells may be applied to any procedure for eucaryotic cell culture including but not limited to microcarrier-based culture, suspension culture, spinner culture, and so-called "roller bottle" culture of cells.

Infection of Producer Cell Line with Virus

In cells which have been infected by multiple copies of a given virus, the activities necessary for viral replication and virion packaging are cooperative. Thus, it is preferred that conditions be adjusted such that there is a significant probability that the producer cells are multiply infected with the virus. An example of a condition which enhances the production of virus in the producer cell is an increased virus concentration in the infection phase. However, it is possible that the total number of viral infections per producer cell can be overdone, resulting in toxic effects to the cell. Consequently, one should strive to maintain the infections in the virus concentration in the range of $10^6$ to $10^{10}$, preferably about $10^9$, virions per ml.

Chemical agents may also be employed to increase the infectivity of the producer cell line. For example, the present invention provides a method to increase the infectivity of producer cell lines for viral infectivity by the inclusion of a calpain inhibitor. Examples of calpain inhibitors useful in the practice of the present invention include calpain inhibitor 1 (also known as N-acetyl-leucyl-leucyl-norleucinal, commercially available from Boehringer Mannheim). Calpain inhibitor 1 was observed to increase the infectivity of producer cell lines to recombinant adenovirus.

III. Culture, Harvest, Lysis and Purification

During the phase where viral replication is proceeding, the bioreactor is continuously fed with serum free supplemented media. Oxygen concentration should be maintained at a level of about 50% to about 120% dissolved oxygen, preferably about 100% dissolved oxygen. In order to maximize the intracellular concentration of viral particles, one should monitor the accumulation of virus particles within the cells. In the preferred method, the viral concentration is determined by HPLC using a Resource Q® column as described in Example 7 herein. When the level of viral particles begins to plateau, the bioreactor is stopped and cells are harvested.

The invention further provides a method of producing intact viral particles comprising the steps (a)–(g) above and further comprising the steps of:

h) harvesting the cells;

i) lysing the producer cells;

j) isolating the viral particles;

k) purifying the intact viral particles.

When the concentration of viral particles is optimized as determined above, the entire contents of the bioreactor are removed and buffered to maintain a pH of approximately pH 7.0 to about 8.5. At this point the cells may be frozen for storage at −70° C.

Lysis and Purification

When it is desired to isolate the viral particles from the producer cells, the cells are lysed, using a variety of means well known in the art. For example, mammalian cells may be lysed under low pressure (100–200 psi differential pressure) conditions or conventional freeze thaw methods. Exogenous free DNA/RNA is removed by degradation with DNAse/RNAse. The viral particles are then purified by means known in the art. Chromatographic or differential density gradient centrifugation methods may be employed. In the preferred practice of the invention, the virus is purified by column chromatography in substantial accordance with the process of Huyghe et al. (1995) *Human Gene Therapy* 6: 1403–1416 as described in co-pending U.S. patent application Ser. No. 08/400,793 filed Mar. 7, 1995.

EXAMPLES

As will be apparent to those skilled in the art to which the invention pertains, the present invention may be embodied in forms other than those specifically disclosed below. The particular embodiments of the invention described in the Examples below, are, therefore to be considered as illustrative and not restrictive of the scope of the present invention.

Example 1

Preparation of microcarriers

Cytodex 1 microcarrier beads were prepared by swelling and hydrating in PBS. The PBS for this procedure was prepared by 1:10 dilution of 10× phosphate buffered saline (PBS) in Milli-Q water (pH 7.5). 10 grams of Cytodex 1 microcarrier beads were added to a clean 500 ml bottle. Approximately 300–400 milliliters of PBS was added to the bottle and the contents were stirred until the microcarriers are completely hydrated and suspended (approximately 3 minutes). The microcarriers were allowed to settle for approximately 10 minutes. The PBS was removed by aspiration. The washing procedure was repeated twice.

The microcarriers were resuspended in a final volume of 300 ml of PBS. The microcarriers were sterilized in an autoclave for 30 minutes at 250° F. The bottle containing the sterile microcarriers was transferred to a laminar flow hood. The PBS was removed by aspiration and the beads washed once as above with sterile PBS. The microcarriers were then washed once in sterile DMEM containing 10% fetal bovine serum (FBS). The microcarriers were resuspended to a final volume of 300 ml with sterile DMEM containing 10% FBS.

Example 2

Preparation of 293 GT Cells 10 ml of sterile DMEM containing 10% FBS was placed in a 15 ml conical tube. A vial of 293 GT cells containing approximately $5 \times 10^6$ cells was obtained from storage under liquid nitrogen and thawed in a water bath at 37° C. The exterior of the vial was washed in 70% isopropanol and opened in a laminar flow hood. The contents of the vial were transferred to the tube containing the media. The tube was then centrifuged at 1,000 RPM in a Beckman TJ6 centrifuge for approximately 5 minutes. The supernatant was then removed by aspiration and the pellet resuspended in 10 ml of media. The suspension was then transferred to a T-225 flask and incubated at 37° C. for approximately 50 hours. The cells were allowed to grow to approximately 50–90% confluence as determined by light microscopy.

Upon reaching sufficient confluency, the medium was removed from the flasks and 10–30 ml of PBS was gently pipetted along the top of the flasks. The flasks were then laid down, coating the cells with PBS. The PBS was removed from the flasks and 10 ml of a 0.05% trypsin solution (0.05% trypsin, 0.53 mM EDTA commercially available from GibcoBRL as catalog No. 25300-054) was added. The flask was gently rocked to ensure that the trypsin solution covered the monolayer. After approximately 45 seconds, each flask was struck sharply until the cells were completely detached from the flask. Immediately, 20 ml of complete medium was added to each flask. The flask contents were pooled via centrifugation (1,000 RPM in a Beckman TJ6 centrifuge for approximately 5 minutes). The supernatant was decanted from the centrifuge tube, triturated and the cells were pooled using complete media. The cell count was determined by use of a Reichert Bright-Line Hemacytometer (Buffalo, N.Y.).

The culture was divided into four T-225 flasks (approximately $5 \times 10^6$ cells per flask). 10 ml of suspension was pipetted into each flask to be seeded. Complete medium was added to each of the flasks to a volume of 50 ml. The cells were incubated at 37° C. in a humidifed 7% carbon dioxide atmosphere. The cells were then expanded using the above procedure to 20 T-225 flasks. This process was repeated until a sufficient quantity of cells was prepared to seed the microcarriers, approximately $6.5 \times 10^8$ cells.

Example 3

Seeding of the Microcarriers

Approximately $6.5 \times 10^8$ human 293 cells prepared in substantial accordance with the teaching of Example 2 above were suspended in 5 liters of Biowhittaker #12-604-F Dulbecco's Modified Eagle's Medium (DMEM) serum containing media (commercially available from Biowhittaker, Inc., Walkersville Md.) and 50 grams of microcarriers prepared in substantial accordance with the teaching of Example 1 above. The above mixture was well agitated by swirling for a period of approximately 2 minutes. The whole mixture was then siphoned into the sterilized clean culture vessel of a CelliGen Plus® 5 liter bioreactor fitted with a Cell-Lift impeller (obtained from New Brunswick Scientific Company, Inc., 44 Talmadge Road, Edison, N.J., U.S.A. 08818-4005).

The cells were then cultured at a temperature 37° C., maintaining a dissolved oxygen concentration of approximately 100%. Dissolved oxygen concentration was monitored and maintained by the use of a dissolved oxygen probe linked to controller (part of the CelliGen Plus bioreactor) so that dissolved oxygen was level was maintained at approximately 100% by sparging with air, $CO_2$, $O_2$ or $N_2$ as appropriate. The culture was maintained under atmospheric pressure and at a pH of approximately 7.2. The vessel is stirred at a rate dependent on the volume of the bioreactor vessel and may range from approximately 15 to 200 rpm. For the 5 liter bioreactor used here, the stirring rate was maintained at approximately 70 rpm. Cells were cultured until the cell density reached the desired level ($8–10 \times 10^6$ cells per milliliter or approximately 230 cells per microcarrier). One may also determine cell density by the rate of oxygen consumption, which is proportional to cell concentration. After approximately 3 days of incubation, the reaction vessel was fed continuously with medium at the rate of approximately 0.5 liters per day per $1 \times 10^6$ cells. The spent medium was removed via a decanting column. The cells were allowed to culture for a period of approximately 14 days.

In order to determine the number of cells per milliliter, the agitation was increased to 100 rpm and a 5 ml sample was quickly drawn out using a sterile syringe. The syringe contents were then transferred to a 15 ml conical tube. When the microcarriers settled, the supernatant was removed by aspiration and replaced with an identical volume of 0.25% trypsin solution (0.25% trypsin, 1 mM EDTA, commercially available from GibcoBRL as Catalog No. 25200-056). The tube was capped and incubated in a 37° C. water bath for approximately 5 minutes (or until cells achieved a bristly appearance on the microcarriers). The tube was then vortexed for 20 seconds and as soon as the microcarriers began to settle (approximately 1 minute, a sample was drawn from above the microcarrier layer for counting by hemacytometer.

Example 4

Media Exchange

Once the cells achieved the desired density, the temperature controller, agitator, and perfusion were turned off and the microcarriers were allowed to settle. Once the microcarriers settled, the medium was removed by siphoning. The reactor was filled with 5 liters of DMEM (without serum or additives. Biowhittaker). The agitation was turned on sufficiently to disrupt the microcarrier/cell cake (approximately 150 rpm) for approximately 3 minutes. The agitation was stopped and the coated microcarriers were allowed to settle. This process was repeated twice. Then the reactor was filled with 5 liters of DMEM containing 1% CMF-1 (Applied Nutrient Sciences, Sorrento Valley Calif.). Agitation was restored to disrupt the cell cake and then set to 70 RPM to maintain suspension of the coated microcarriers. The temperature controller was turned on to maintain a temperature of 37° C.

Example 5
Infection of 293 Packaging Cell Line with Recombinant Adenovirus (ACN53)

$5 \times 10^{12}$ particles of recombinant adenovirus (ACN53 described in Wills, et al (1994) Human Gene Therapy) were added to the culture vessel prepared in Example 4 above. Perfusion was restored as in Example 3 above. After approximately 20 hours of incubation, the reaction vessel was sampled for virus concentration. This was achieved by increasing the agitation to 100 rpm and quickly drawing out a 5 ml sample using a sterile syringe. The syringe contents were then transferred to a 15 ml conical tube. 0.5 ml of a HSM buffer (50 mM Hepes, 3% sucrose, 2 mM $MgCl_2$, 150 mM NaCl, and 5% beta-cyclodextrin, pH 7.5) was added. The tube was then frozen in liquid nitrogen and quickly thawed in a 10° C. water bath. This freeze/thaw process was repeated twice. The tubes were centrifuged at 3,000 RPM in a Beckman TJ6 centrifuge for approximately 5 minutes. A sample of supernatant was drawn and determined by the Resource Q® assay as described by Shabram, et al. (1996–7) Human Gene Therapy. This process was repeated periodically (approximately every 2 hours) until it was determined that the viral concentration began to drop (i.e. the optimal viral concentration had been acheived). The results are presented in data is presented in Table 1 below and a graphical representation of the data is provided in FIG. 2 of the attached drawings.

TABLE 1

Production of ACN53 in 293 GT Cells

| Hours Post Infection | PN/ml | Total PN |
|---|---|---|
| 24 | $1.12 \times 10^{10}$ | $5.58 \times 10^{13}$ |
| 32 | $2.67 \times 10^{10}$ | $1.33 \times 10^{14}$ |
| 38 | $4.61 \times 10^{10}$ | $2.30 \times 10^{14}$ |
| 46 | $4.34 \times 10^{10}$ | $2.17 \times 10^{14}$ |
| 47 | $4.36 \times 10^{10}$ | $2.18 \times 10^{14}$ |
| 48.5 | $4.62 \times 10^{10}$ | $2.31 \times 10^{14}$ |
| 49.5 | $6.38 \times 10^{10}$ | $3.19 \times 10^{14}$ |
| 50.5 | $5.23 \times 10^{10}$ | $2.61 \times 10^{14}$ |
| 51.5 | $5.02 \times 10^{10}$ | $2.51 \times 10^{14}$ |
| 52.75 | $5.77 \times 10^{10}$ | $2.89 \times 10^{14}$ |
| 53.75 | $5.74 \times 10^{10}$ | $2.87 \times 10^{14}$ |
| 54.75 | $5.15 \times 10^{10}$ | $2.57 \times 10^{14}$ |

As can be seen from the data presented above, for ACN53 the optimal viral concentration is achieved approximately 50 hours post infection, although this will vary with individual constructs. The contents of the vessel were removed to freezer safe containers and mixed with 10–20% HSM buffer and frozen.

Example 6
Harvest and Lysis of Infected Cells

The whole contents containing the cells were lysed by a repeated freeze/thaw procedure. The contents were frozen in a −80° C. freezer and thawed in a water bath at room temperature. The virus was purified in substantial accordance with the process of Huyghe et al. (1995) *Human Gene Therapy* 6: 1403–1416.

Example 7
Production of ACN-Rb110

The process described in Examples 1–5 was repeated except that a recombinant adenovirus expressing the p110 retinoblastoma protein (ACNRb110) was used to infect the 293 cells. Construction of the ACNRB110 adenovirus is described in Smith, et al. (1997) Circulation 96:1899–1905. The cell density at the time of infection was $1.0 \times 10^7$ cells/ml. The results of the infection culture are presented in FIG. 3 of the attached drawings. In this example, a viral titer of approximately 39,000 viral particles per cell was achieved.

Example 8
Improvement of Viral ACN-p53 Viral Titer Using N-acetyl-L-cysteine

A culture of 293 producer cells is prepared in substantial accordance with the teaching of examples 1–4 above. Cells are infected with ACN53 adenoviruses as described in Example 5. However, the procedure of Example 5 is modified by the addition of N-acetyl-L-cysteine to a final concentration of approximately 10–30 mM in the culture media to inhibit the CMV promoter. The cells are cultured and harvested in substantial accordance with the teaching of Examples 5 and 6. Improved intracellular concentration of viral particles results from the inhibition of expression of the p53 transgene.

We claim:

1. A method of achieving a cell density greater than $5 \times 10^6$ producer cells/ml in a microcarrier based bioreactor process for the production of a virus in a producer cell, said method comprising the steps of:
   a) preparing a culture of producer cells attached to microcarriers wherein the ratio of producer cells to microcarriers is approximately 10 cells/microcarrier
   b) seeding the bioreactor with a quantity of the producer cell-coated microcarriers prepared in step (a) to a density greater than approximately 6 grams (based on the dry weight of the microcarrier) of producer cell-coated microcarriers per liter of bioreactor media volume; and
   c) culturing the producer cells in the bioreactor under perfusion conditions in serum containing media to a density of greater than 100 cells/microcarrier.

2. The method of claim 1, wherein the producer cell is a 293 cell.

3. The method of claim 2 wherein the virus is an adenovirus.

4. The method of claim 3 wherein the virus is a replication defective adenovirus derived from the adenovirus type 5 genome.

5. The method of claim 4 wherein the replication defective adenovirus further comprises an expression cassette for an exogenous transgene.

6. The method of claim 5 wherein the exogenous transgene is selected from the group consisting of tumor suppressor genes, cytotoxic genes, cytostatic genes, proapoptotic genes, or prodrug activating genes.

7. The method of claim 6 wherein the exogenous transgene is a tumor suppressor gene.

8. The method of claim 7 wherein the tumor suppressor gene is p53.

9. A method producing a population of producer cells containing a high titer of viral particles in a microcarrier based bioreactor in serum free media, said method comprising the process of claim 1 further comprising the steps of:
   d) removing the serum containing medium;
   e) synchronizing the producer cells in G1 phase;
   f) infecting the producer cells with a virus;
   g) culturing cells under conditions to permit viral replication until a maximum point is achieved.

10. The method of claim 9, wherein the producer cell is a 293 cell.

11. The method of claim 10 wherein cell synchronization is achieved by holding the cells in a non-serum medium for greater than approximately one-third of a cell cycle.

12. The method of claim 11 wherein the virus is an adenovirus.

13. The method of claim 12 wherein the virus is a replication defective adenovirus derived from the adenovirus type 5 genome.

14. The method of claim 13 wherein the replication defective adenovirus further comprises an expression cassette for an exogenous transgene.

15. The method of claim 14 wherein the exogenous transgene is selected from the group consisting of tumor suppressor genes, cytotoxic genes, cytostatic genes, proapoptotic genes, or prodrug activating genes.

16. The method of claim 9, further comprising the steps of:

h) harvesting the cells;

i) lysing the producer cells;

j) isolating the viral particles from the cell lysate; and k) purifying the intact viral particles.

17. The method of claim 11 wherein the virus is an adenovirus.

* * * * *